United States Patent
Tsaclas (10) Patent No.: US 9,192,201 B1
(45) Date of Patent: Nov. 24, 2015

(54) IMPLANTED PORT PROTECTION DEVICE (71) Applicant: Patient Port Protection, Inc., West Islip, NY (US)

(72) Inventor: Stephen Thomas Tsaclas, Coral Springs, FL (US)

(73) Assignee: Patient Port Protection, Inc., West Islip, NY (US)

( * ) Notice: Subject to any disclaimer, the term of this patent is extended or adjusted under 35 U.S.C. 154(b) by 0 days.

(21) Appl. No.: 14/512,409

(22) Filed: Oct. 11, 2014

(51) Int. Cl.
*A41D 13/12* (2006.01)
*A61M 39/02* (2006.01)

(52) U.S. Cl.
CPC ....... *A41D 13/1236* (2013.01); *A61M 39/0208* (2013.01); *A61M 2209/088* (2013.01)

(58) Field of Classification Search
CPC ............ A41D 13/015; A41D 13/0518; A41D 13/0587; A41D 13/0593; A61F 15/008
See application file for complete search history.

(56) References Cited

U.S. PATENT DOCUMENTS

| | | | | |
|---|---|---|---|---|
| 4,241,459 | A * | 12/1980 | Quayle | 2/102 |
| 4,441,211 | A * | 4/1984 | Donzis | 2/459 |
| 4,831,666 | A * | 5/1989 | Denman | 2/23 |
| 5,245,706 | A | 9/1993 | Moschetti et al. | |
| 5,621,914 | A * | 4/1997 | Ramone et al. | 2/463 |
| 6,320,093 | B1 * | 11/2001 | Augustine et al. | 602/41 |
| 8,220,079 | B2 | 7/2012 | Syska et al. | |
| 2007/0197983 | A1 * | 8/2007 | Giles Finn | 604/347 |
| 2007/0199129 | A1 * | 8/2007 | Davis | 2/69 |
| 2008/0202531 | A1 * | 8/2008 | Fletcher | 128/888 |
| 2009/0126087 | A1 * | 5/2009 | Armstrong et al. | 2/455 |
| 2011/0023218 | A1 | 2/2011 | Syska et al. | |
| 2011/0056004 | A1 * | 3/2011 | Landi | 2/459 |
| 2013/0184630 | A1 * | 7/2013 | Sundaresh | 602/43 |
| 2014/0259324 | A1 * | 9/2014 | Behrend et al. | 2/455 |
| 2014/0283850 | A1 * | 9/2014 | Suarez et al. | 128/888 |

* cited by examiner

*Primary Examiner* — Shaun R Hurley
*Assistant Examiner* — Andrew W Sutton
(74) *Attorney, Agent, or Firm* — Gerard M. Wissing (57) ABSTRACT

Protective devices and systems for covering surgically implanted ports are provided. More specifically, the present disclosure relates to protective devices and systems configured to protect a surgically implanted port from damage during daily physical activities, daily athletic activities and in the unfortunate event of an accidental impact to the body area where the port is implanted.

14 Claims, 11 Drawing Sheets

IMPLANTED PORT PROTECTION DEVICE

BACKGROUND

1. Field

The present disclosure relates to protective devices for covering a surgically implanted port. More specifically, the present disclosure relates to protective devices configured to protect a surgically implanted port from damage during daily physical activities, daily athletic activities and in the unfortunate event of an accidental impact to the body area where the port is implanted.

2. Description of the Related Art

Patients undergoing the treatment of certain medical conditions may be required to endure repeated needle sticks to aid in the treatment of the patient. For example, patients with certain medical conditions endure repeated injections of drugs to treat the condition, or repeated drawing of blood samples to ensure the treatment is working. To ease patient discomfort associated with repeated needle sticks, patients may elect to have a port, or combined port and catheter, also called a "portacath," surgically implanted beneath the skin. Other terms commonly used in the medical field for ports and portacaths include "totally implantable venous access system" and "central venous access devices." For the present disclosure, reference to "ports" includes ports, portacaths, totally implantable venous access system and central venous access devices. Ports have many different uses, such as total parenteral nutrition, delivery of chemotherapy, delivery of coagulation factors, the withdrawing of blood from patients requiring frequent blood tests, delivery of antibiotics, and the delivery of various medications.

Figure 1:
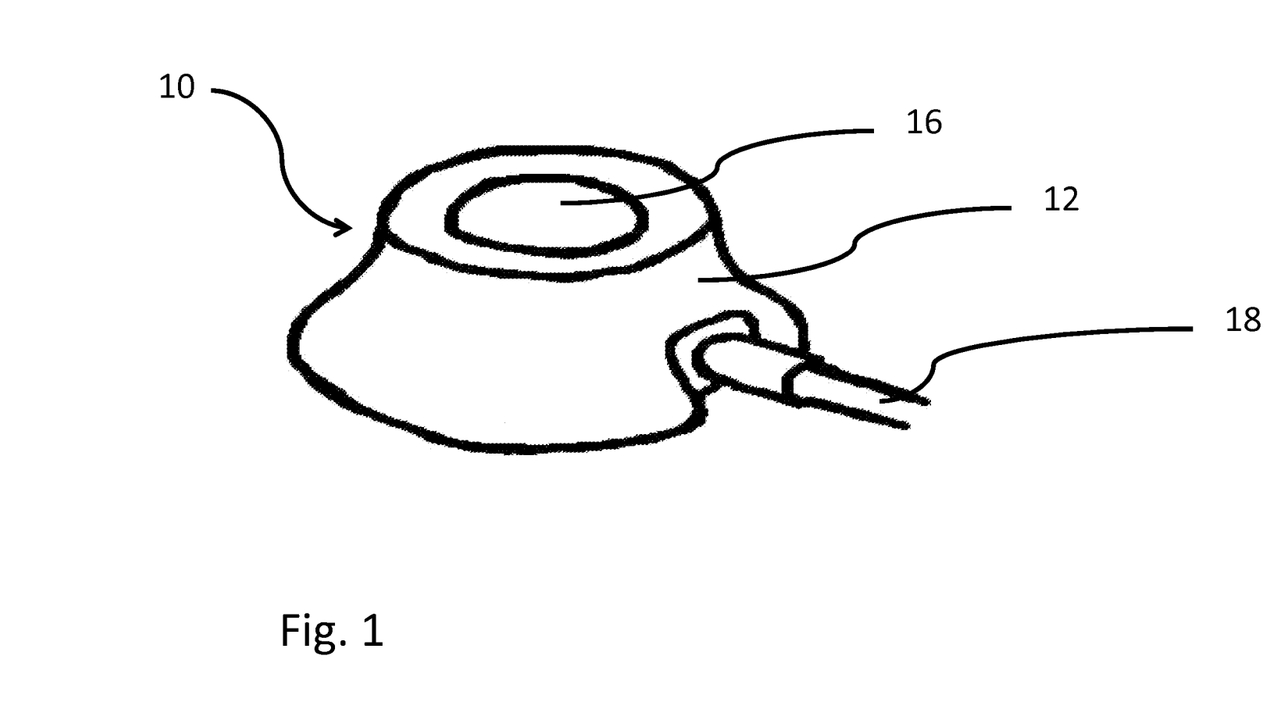
FIG. 1 is a perspective view of a surgically implantable port.
Figure 2:
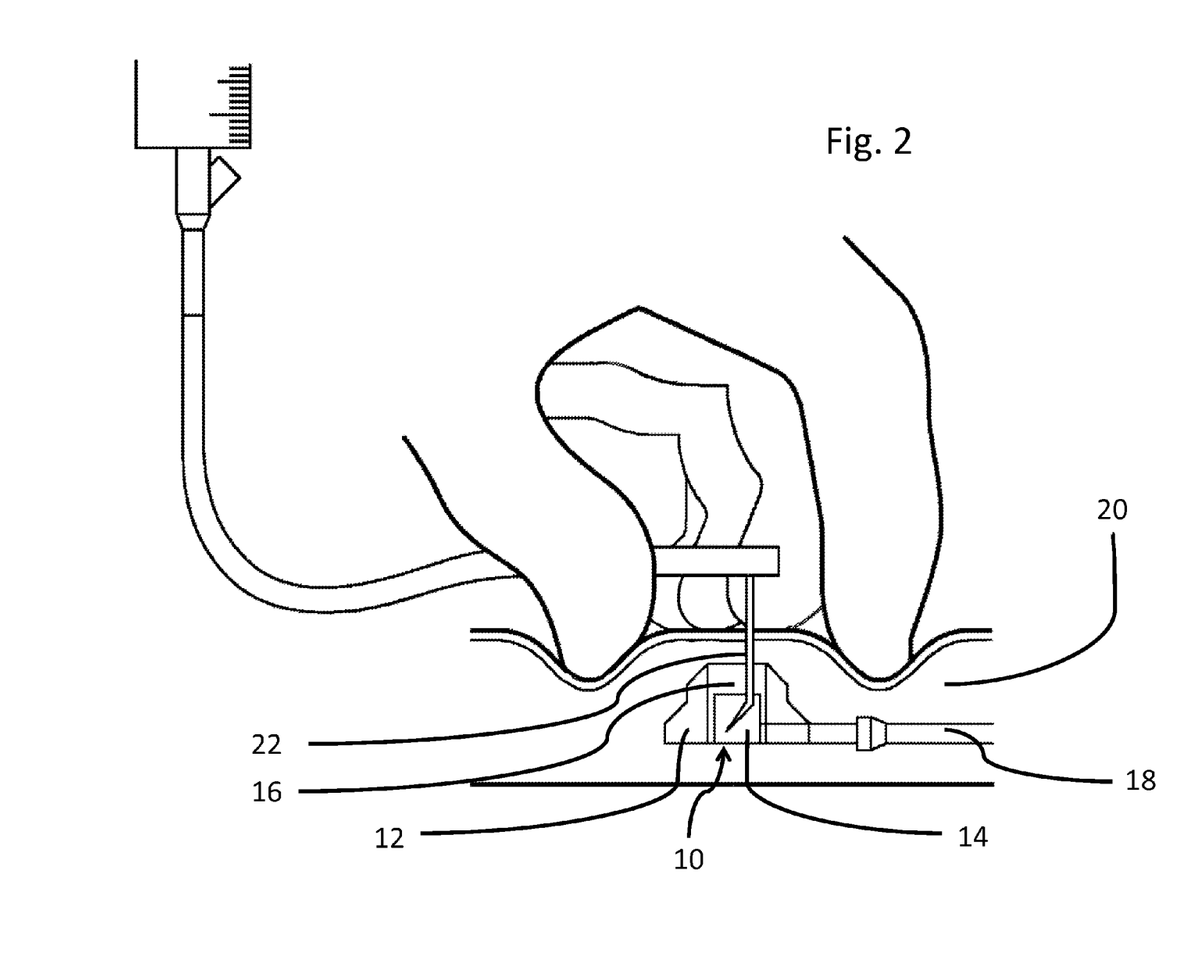
FIG. 2 is a side view of a port implanted within the body and illustrating a needle inserted into the port.

As seen in FIGS. 1 and 2, a port 10 has a housing 12 with an interior reservoir compartment (or portal) 14 that has a silicone bubble (or septum) 16 for needle insertion, and a catheter or an attached plastic tube 18. The septum 16 is made out of a self-sealing silicone rubber and can be punctured many times before it weakens significantly.

Figure 3:
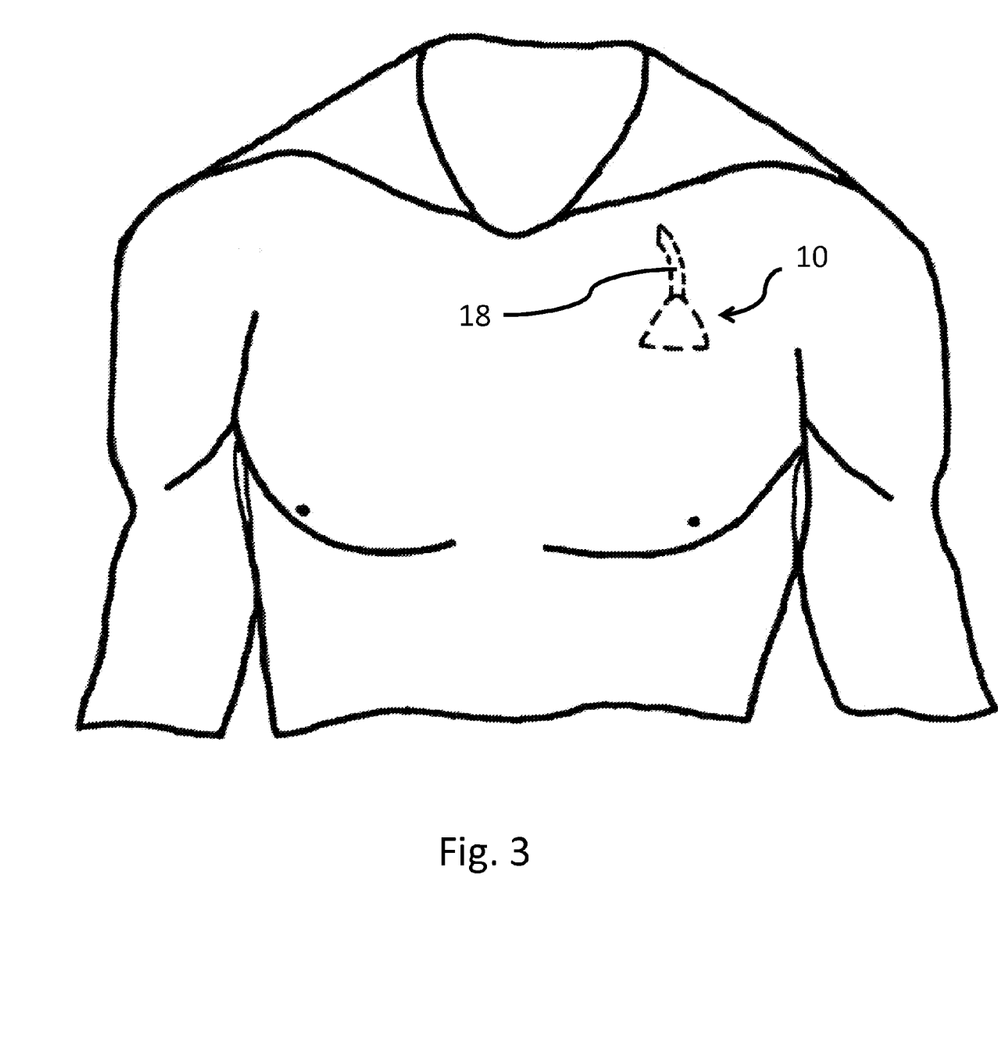
FIG. 3 illustrates a body with a port implanted under the skin in the upper chest area of the body.

The port 10 is surgically implanted just beneath the skin 20, typically in the upper chest (as seen in FIG. 3) or in the aim, and appears as a bump under the skin. However, the port may be implanted in other areas of the body, such as the upper leg. The catheter 18 runs from the portal 14 and is surgically inserted into a vein, usually the jugular vein, the subclavian vein, or the superior vena cava. Referring to FIG. 2, to administer treatment or to withdraw blood, the port 10 is located and the area is disinfected. The port 10 is then accessed by puncturing the overlaying skin with needle 22 and inserting the needle into a septum 16. This can be done many times with less patient discomfort. When the port 10 is no longer needed, the port can be removed through a surgical operation.

Since the port is surgically implanted under the skin, there is a risk that patients may damage the port during the course of routine daily activities, physical activities, especially for sports activities, or even in the event of an accidental fall. During such activities, people who have a port sometimes experience pain when physical contact is made with their port. Persons with a port are also at a risk of rupturing the structural sutures that hold the port in place. It is also possible that the catheter may be ruptured or torn loose, or that the port itself may be damaged upon impact.

It would be advantageous to have a protective device for a port that is shaped and sized to protect the port from damage, and that is capable of being located at any position on the body of a patient with such a port. It would also be advantageous, to have an article of clothing to position and hold the protective device in place while also allowing access to the port during treatment.

BRIEF DESCRIPTION OF THE DRAWINGS

The features of the present disclosure will be more readily apparent from the following detailed description and drawings of the illustrative embodiments in which.

SUMMARY

The present disclosure provides embodiments for a protective device for surgically implanted ports. In one embodiment, the protective device includes a port shield having an arched structure with a crown and at least two side supports, and at least one impact absorption layer positioned at least partially along a perimeter of the port shield. In this configuration, energy from an impact to the port shield is dissipated along a surface of the port shield to the at least two side supports and is at least partially absorbed by the at least one impact absorption layer. Preferably, the port shield is made of plastic, and the at least one impact absorption layer is made of foam.

In another embodiment, the protective device includes a port shield having an arched structure with a crown and at least two side supports, a padded layer secured to an inner surface of the port shield, and at least one impact absorption layer positioned at least partially along a perimeter of the padded layer. In this configuration, energy from an impact to the port shield is dissipated along a surface of the port shield to the at least two side supports and is at least partially absorbed by the padded layer and the at least one impact absorption layer. Preferably, the port shield is made of plastic, the at least one impact absorption layer and the padded layer are made of foam.

In another embodiment, a protective system for surgically implanted ports is provided. In this embodiment, the protective system includes a port shield having an arched structure with a crown and at least two side supports, and a compartment having a sleeve configured and dimensioned to receive the port shield. At least two impact absorption members positioned within the compartment such that one impact absorption member is adjacent one side support and between a body when worn by a patient and the port shield. Preferably, the compartment has a cover.

In this embodiment, the port shield is made of plastic, and the compartment is made of a material used to fabricate garments. Preferably, the compartment is attached to a garment, and the compartment material is the same as the material used to fabricate the garment. Alternatively, the compartment can be integrally formed into the garment. Preferably, the compartment has a window to permit access to an area of a body when worn.

DETAILED DESCRIPTION

Figure 4A:
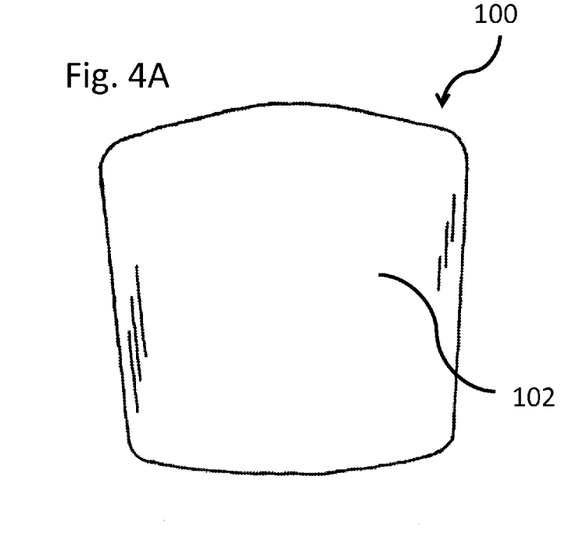
FIG. 4A is a front view of a protective device in accordance with one embodiment of the present disclosure.
Figure 4B:
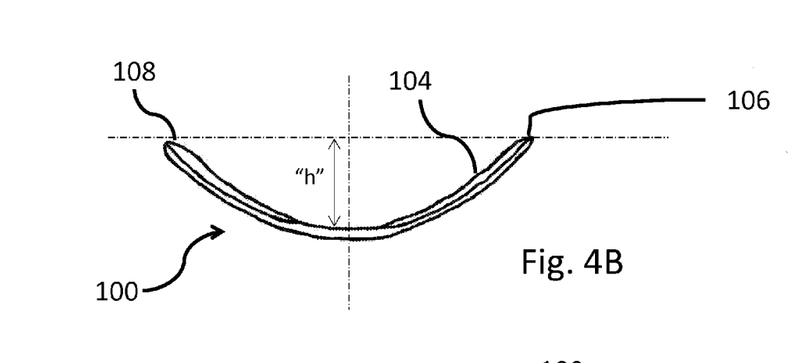
FIG. 4B is a top view of the protective device of FIG. 4A.
Figure 4C:
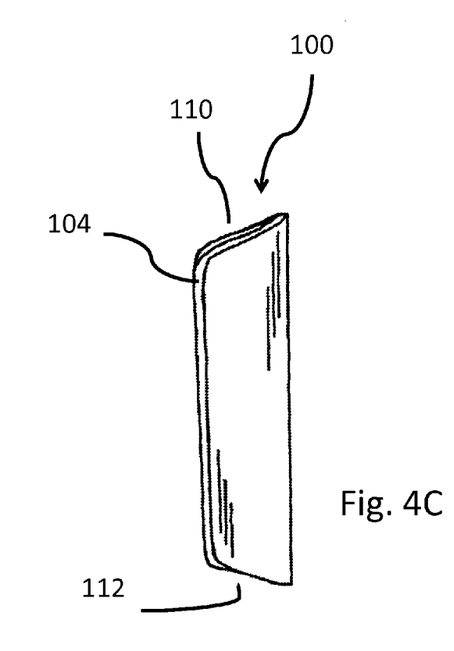
FIG. 4C is a side view of the protective device of FIG. 4A.

Referring to FIGS. 4A-4C, an embodiment of the protective device according to the present disclosure is provided. In this embodiment, the protective device 100 has a port shield 102 and one or more impact absorption layers 104. The port shield 102 is preferably lightweight and rigid or semi-rigid such that it can flex when impacted to reduce the force of the impact on the body and return to its original shape. The port shield 102 may be formed of plastic, polymers, aluminum, composite materials such as carbon fiber, hardened rubber, or any other material or combination of materials capable of withstanding an impact caused during daily physical activities, daily athletic activities and in the unfortunate event of accidental impacts.

Figure 6:
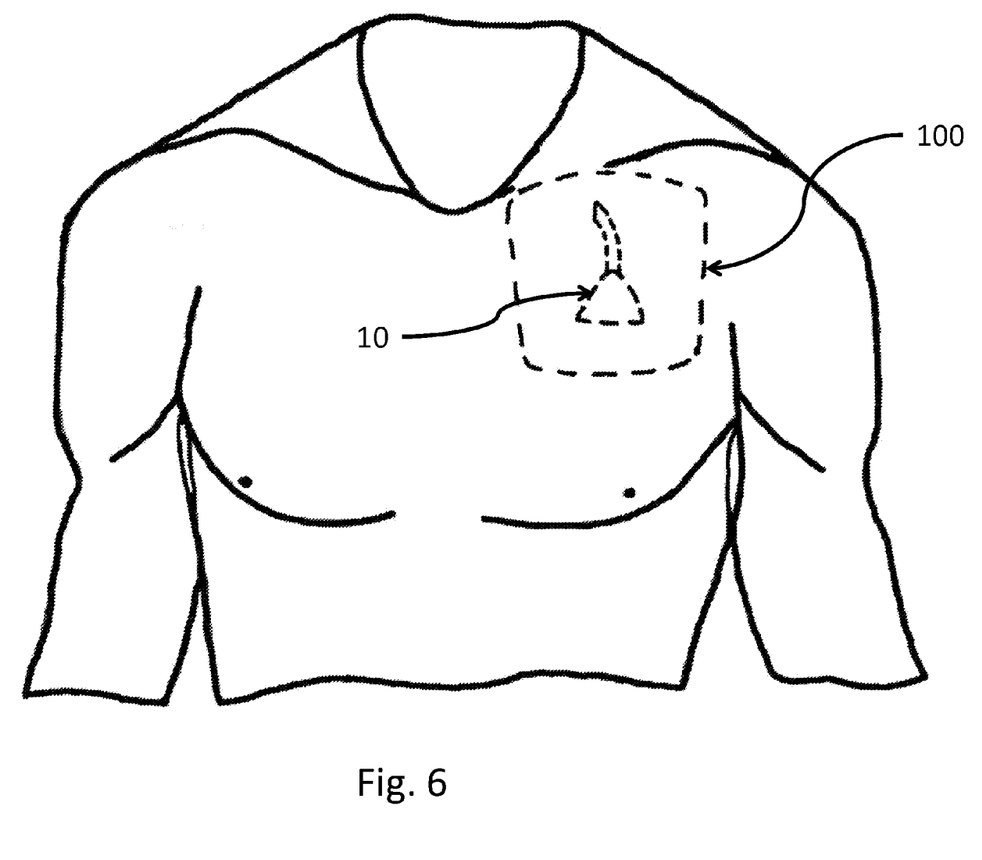
FIG. 6 illustrates a body with a port implanted under the skin in the upper chest area, and a protective device according to an embodiment of the present disclosure positioned over the port.

The port shield 102 is dimensioned with a length and width so as to extend beyond the periphery of an implanted port (as seen in FIG. 6), and preferably fits tightly within a compartment (described below) that positions the protective device 100 relative to an implanted port 10. An example of a suitable length range is between about 4 inches and about 6 inches, and an example of a suitable width range is between about 4 inches and about 6 inches. The port shield 102 is preferably an arched structure (seen in FIG. 4B) that may be, for example, a parabolic or curved arch with two side support surfaces 106 and 108 and a height "h" at the crown of the arch that is of a sufficient distance such that upon an impact to the port shield 102 the shield may flex but not touch the body. An example of a suitable height range is between about 1 and about 2 inches, and preferably about 1⅜ inches. In this embodiment, the port shield 102 has an open top 110 and open bottom 112 that due to the arched structure do not contact the body. This open top and bottom configuration, where the port shield extends over the region of the body where the port 10 is located such that the protective device 100 does not touch the body in the area near where the catheter 18 is located, minimizes potential damage to the catheter 18 in the area near the port housing 12 from an impact to the port shield 102.

In the embodiment of FIGS. 4A-4C, the one or more impact absorption layers 104 extends at least along an inner perimeter of the port shield 102, and is made of a compressible material, such as foam, foam covered by a cloth material, or any similar material or combination of materials that can compress and absorb an impact against port shield 102.

In this embodiment, in the event of an impact to the port shield 102, energy will be dissipated from the impact region along the surface of the arched structure of the port shield 102 to the side support surfaces 106 and 108, and through the impact absorption layer 104 to the body at points away from the port 10.

Figures 5A, 5B, 5C:
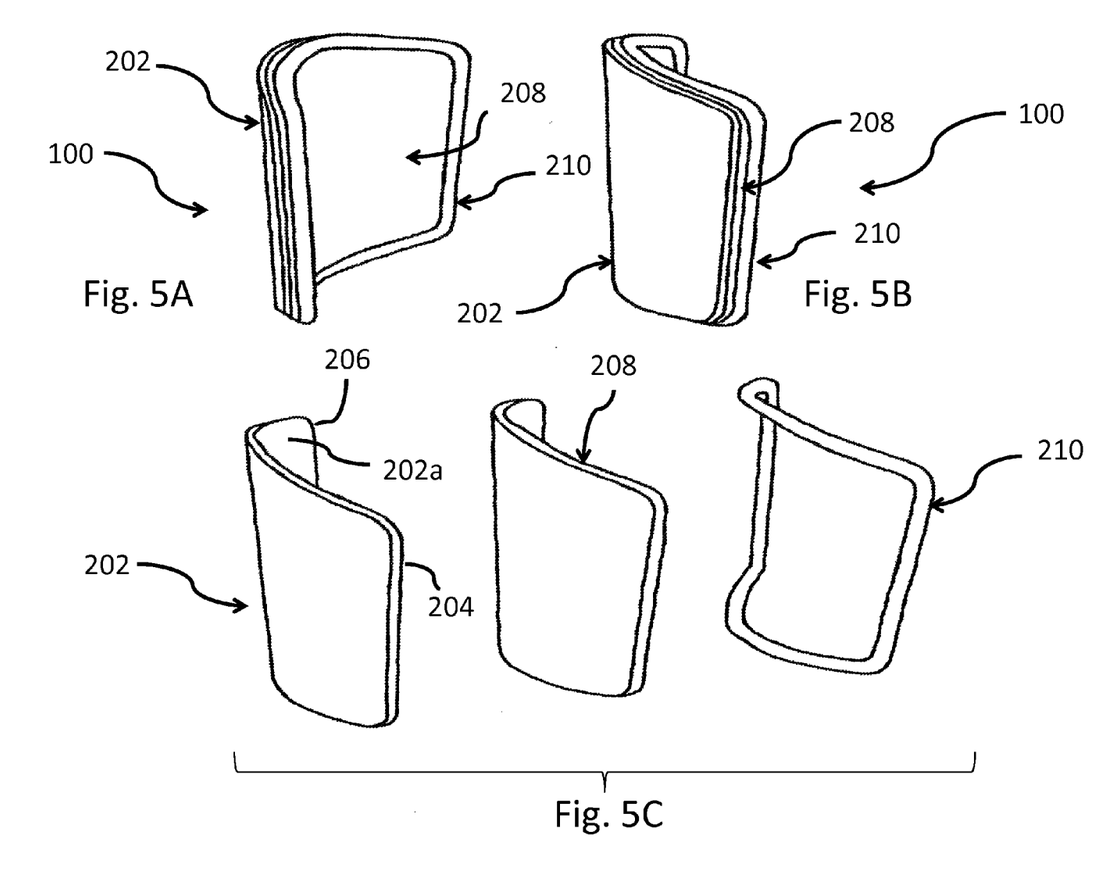
FIG. 5A is a rear perspective view of a protective device in accordance with another embodiment of the present disclosure.
FIG. 5B is a front perspective view of the protective device of FIG. 5A.
FIG. 5C is a front perspective view with parts separated of the protective device of FIG. 5A.

Referring now to FIGS. 5A-5C, another embodiment of the protective device according to the present disclosure is provided. In this embodiment, the protective device 100 has a port shield 202, which is similar to the port shield 102 of FIGS. 4A-4C described above, a padded layer 208, and an impact absorption layer 210. The port shield 202 is preferably lightweight and rigid or semi-rigid such that it can flex when impacted to reduce the force of the impact on the body and return to its original shape. The port shield 202 may be formed of plastic, nylon, polymers, aluminum, composite materials such as carbon fiber, hardened rubber, or any other material or combination of materials capable of withstanding an impact caused during daily physical activities, daily athletic activities and in the unfortunate event of accidental impacts.

The port shield 202 is dimensioned with a length and width so as to extend beyond the periphery of an implanted port, and preferably fits tightly within a compartment (described below) that positions the protective device 100 relative to an implanted port 10. An example of a suitable length range is between about 4 inches and about 6 inches, and an example of a suitable width range is between about 4 inches and about 6 inches. Similar to the embodiment of FIG. 4A-4C, the port shield 202 is preferably an arched structure (seen in FIG. 5C) that may be, for example, a parabolic or curved arch with two side support surfaces 204 and 206 and a height "h" at the crown of the arch that is of a sufficient distance such that upon an impact to the port shield 202 the shield may flex but not touch the body. An example of a suitable height range is between about 1 and about 2 inches, and preferably about 1⅜ inches. In this embodiment, the port shield 202 has an open top 212 and open bottom 214 that due to the arched structure do not contact the body. This open top and bottom configuration, where the port shield extends over the region of the body where the port 10 is located such that the protective device 100 does not touch the body in the area near where the catheter 18 is located, minimizes potential damage to the catheter 18 in the area near the port housing 12 from an impact to the port shield 202.

The padded layer 208 is secured to an interior surface 202a of the port shield 202 and provides an added layer of padding to protect the body and port in the event of an impact to the port shield 202. The padded layer 204 is preferably made of a compressible material, such as foam, foam covered by a cloth material, or any similar material or combination of materials that can compress in the event the port shield is impacted and flexes to a point where a portion of the protective device other than sides impacts the body to provide additional protection to the user, i.e., the patient.

The impact absorption layer 210 extends at least along an inner perimeter of the padded layer 208, and is made of a compressible material, such as foam, foam covered by a cloth material, or any similar material or combination of materials that can compress and absorb an impact against port shield 202.

In this embodiment, in the event of an impact to the port shield 202, energy will be dissipated from the impact region along the surface of the arched structure of the port shield 202 to the side support surfaces 204 and 206, and through at least a portion of the padded layer 208, and through the impact absorption layer 210 to the body at points away from the port 10.

Figure 7:
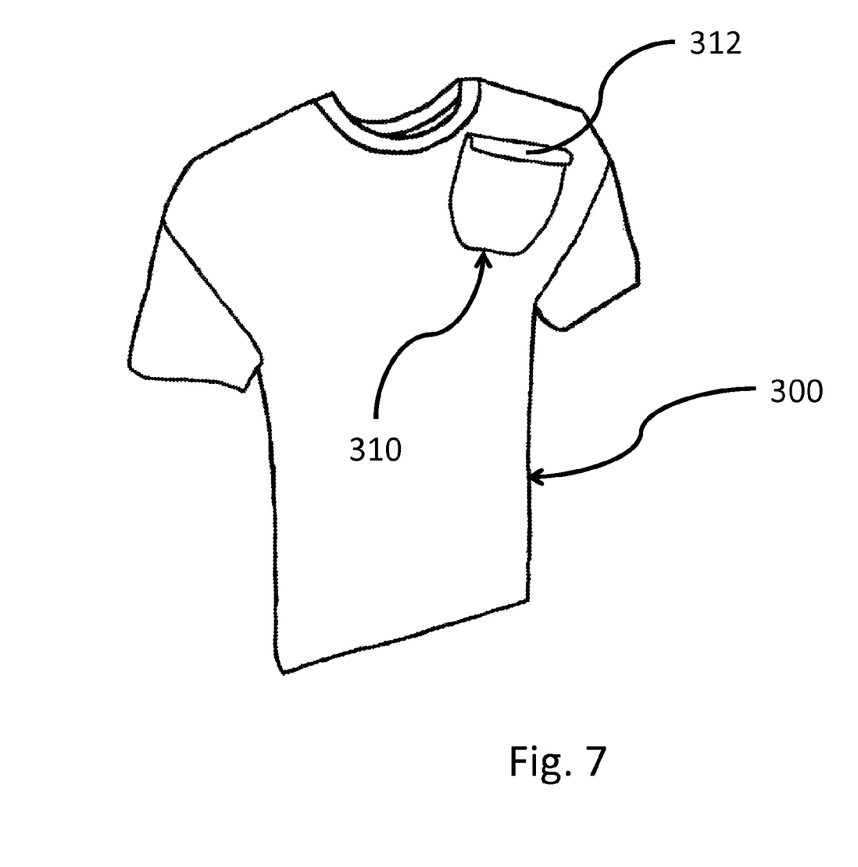
FIG. 7 illustrates an article of clothing having a compartment for holding the protective device.
Figure 8:
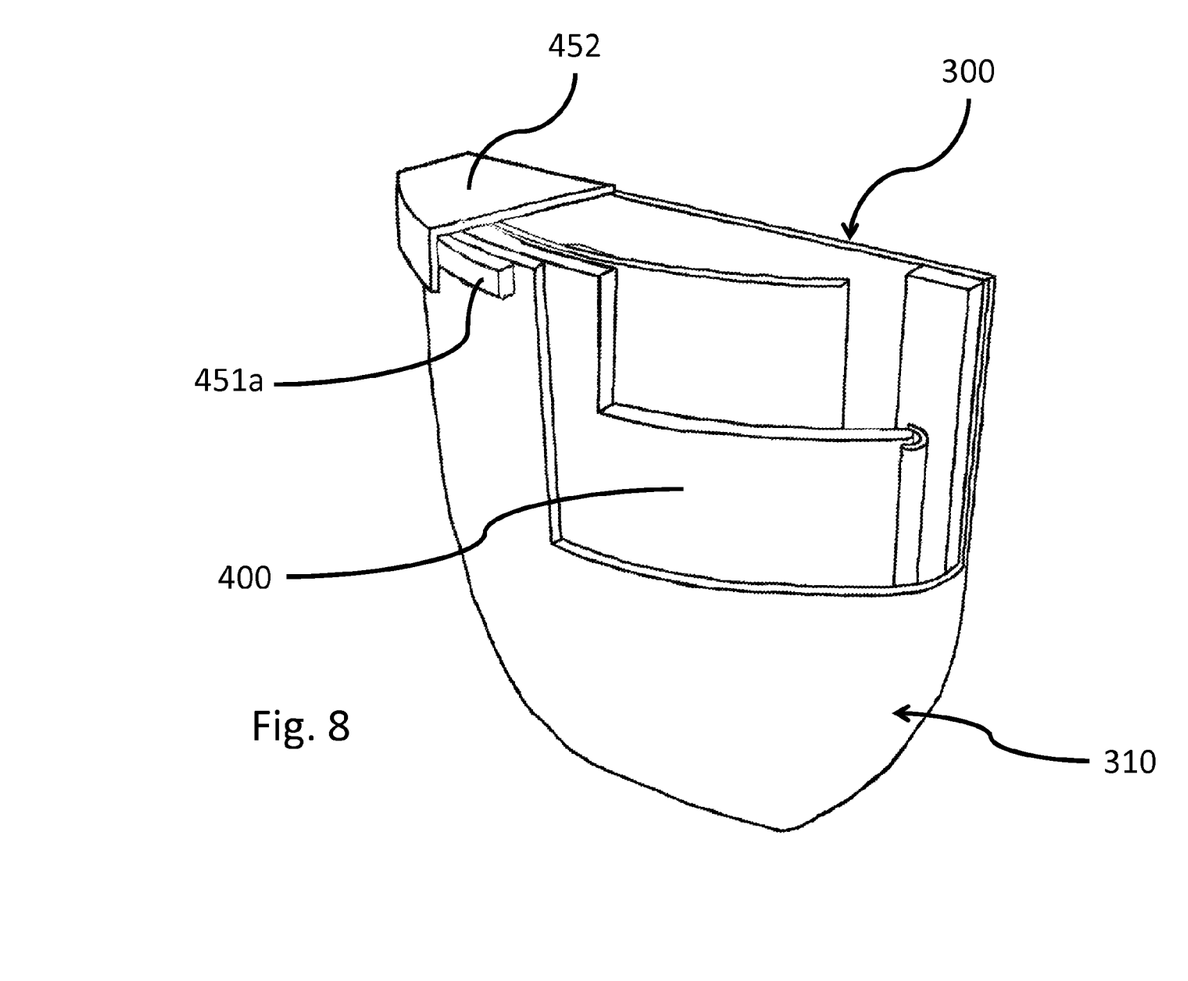
FIG. 8 is a perspective view of another embodiment of the compartment of FIG. 7, illustrating the protective device installed within the compartment.

To position the protective device 100 relative to the port 10, a garment having a compartment may be used. In one embodiment, seen in FIG. 7, the garment is a shirt 300 having a compartment 310, e.g., a covered pocket, which is located on the shirt at a position where ports are typically implanted in a body, here the upper chest region of the body. The compartment 310 has a cover 312 that further limits movement of the protective device 100 when inserted into the compartment 300. The cover 312 may be removably secured to the compartment 310 such that the cover can be opened and closed. Conventional removable securing techniques, such as ® hooks and loops, may be used to removably secure the cover to the compartment. The compartment may be made of the same material as used to fabricate the garment, or it may be made of a material that is different from the material used to fabricate the garment.

Referring now to FIGS. 8-11, an embodiment for a combination protective device 100 compartment 310 and garment 300 used to tightly position the protective device 100 relative to an implanted port 10 is provided. In this embodiment, the protective device 100 includes a port shield 400 that is configured and dimensioned to tightly fit within a compartment 310 in the garment 300. Similar to the embodiments described above, the port shield 400 is preferably an arched structure (seen in FIG. 9) that may be, for example, a parabolic or curved arch with two side support surfaces 402 and 404 and a height "h" at the crown of the arch that is of a sufficient distance such that upon an impact to the port shield 400 the shield may flex but not touch the body. Similar to the embodiments described above, the port shield 400 has an open top and open bottom that due to the arched structure do not contact the body. This open top and bottom configuration, where the port shield extends over the region of the body where the port 10 is located such that the protective device 100 does not touch the body in the area near where the catheter 18 is located, minimizes potential damage to the catheter 18 in the area near the port housing 12 from an impact to the port shield 400.

The garment 300 has a compartment 450, e.g., a covered pocket, that is secured to or located on the garment at a position where ports are typically implanted in a body, e.g., the upper chest region of the body. In this embodiment, the compartment 310 has a cover 452 that further limits movement of the protective device 100 when inserted into the compartment 310. The cover 452 may be removably secured to the compartment 310 such that the cover can be opened and closed. Conventional removable securing techniques, such as Velcro® hooks 451a (seen in FIG. 8) and Velcro® loops 451b (seen in FIG. 10), may be used to removably secure the cover to the compartment.

The compartment 310 has a sleeve 454 formed by an inner sleeve member 456 and an outer sleeve member 458 forming an outer surface of the compartment 310. The outer surface of the compartment 310 is secured to the garment 300 at ends 458a and 458b of the outer sleeve member 458. Typically, the ends 458a and 458b are sewn onto the garment. However, one skilled in the art will recognize a number of other techniques that may be employed to secure the compartment to the garment. The sleeve 454 is configured to receive the port shield 400, as seen in FIG. 9.

Figure 9:
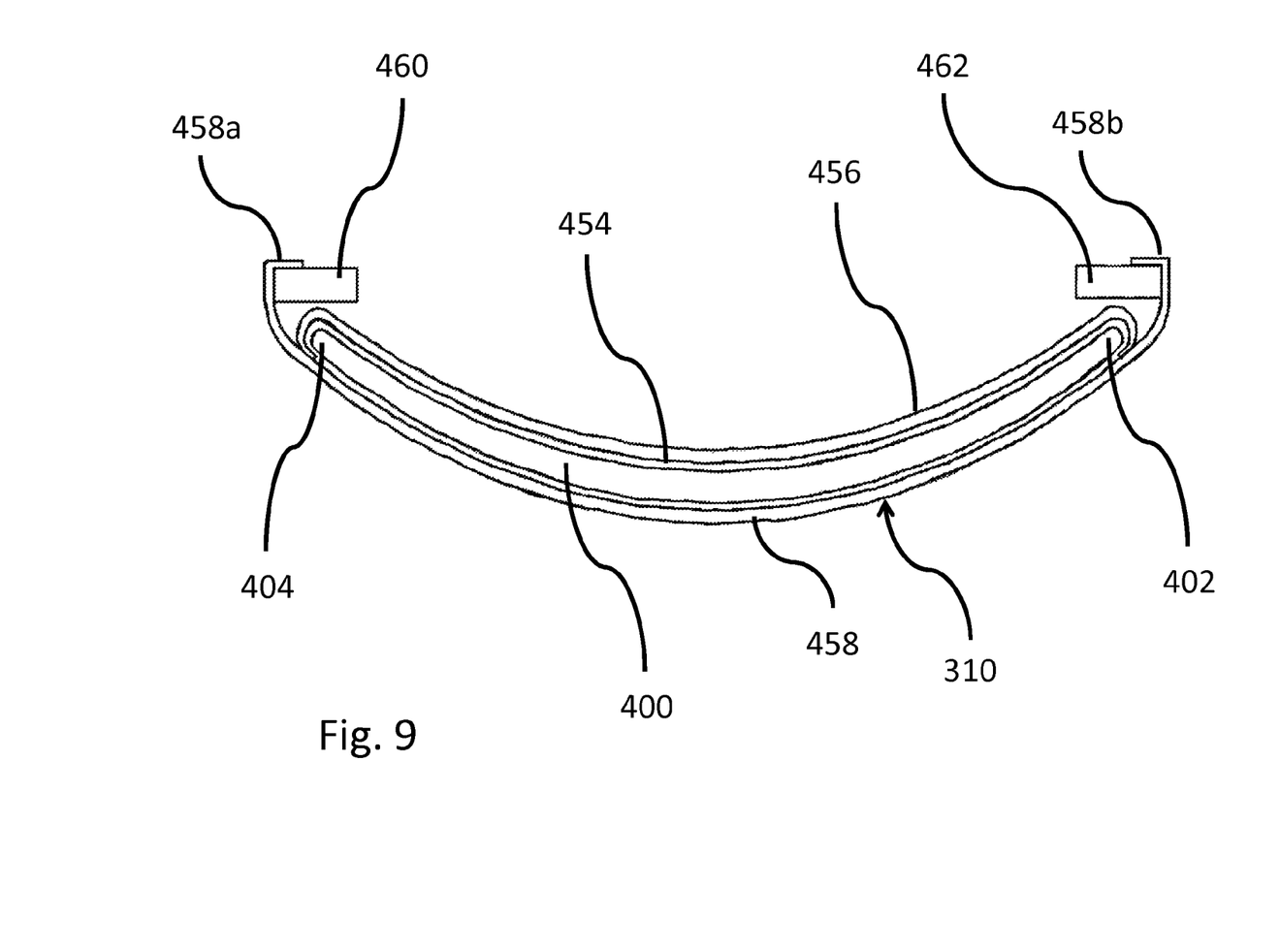
FIG. 9 is a top view of the compartment of FIG. 8.

Within the compartment 310 are impact absorption members 460 and 462 positioned to engage side support surfaces 402 and 404, as shown in FIG. 9. In this configuration, energy due to an impact on the port shield 400, dissipates from the impact region along the surface of the arched structure of the port shield 400 to the side support surfaces 402 and 404, and is at least partially absorbed by the impact absorption members 460 and 462 prior to passing to the body area adjacent to the impact absorption members. The impact absorption members 460 and 462 are made of a compressible material, such as foam, foam covered by a cloth material, or any similar material or combination of materials that can compress and absorb an impact against port shield 400.

Figure 10:
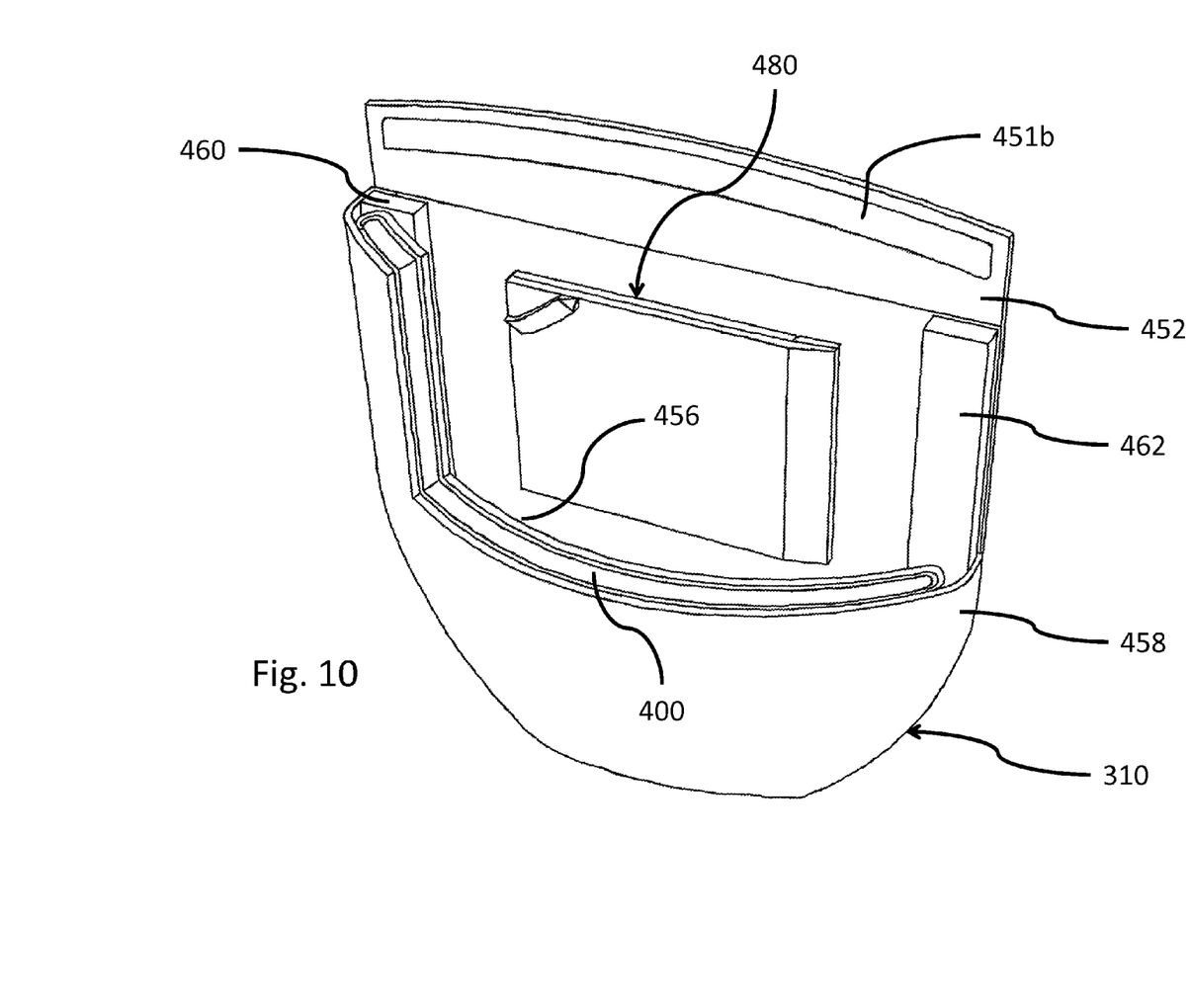
FIG. 10 is a perspective view of the compartment of FIG. 8 with a portion cut away to illustrate an interior window in a closed position.
Figure 11:
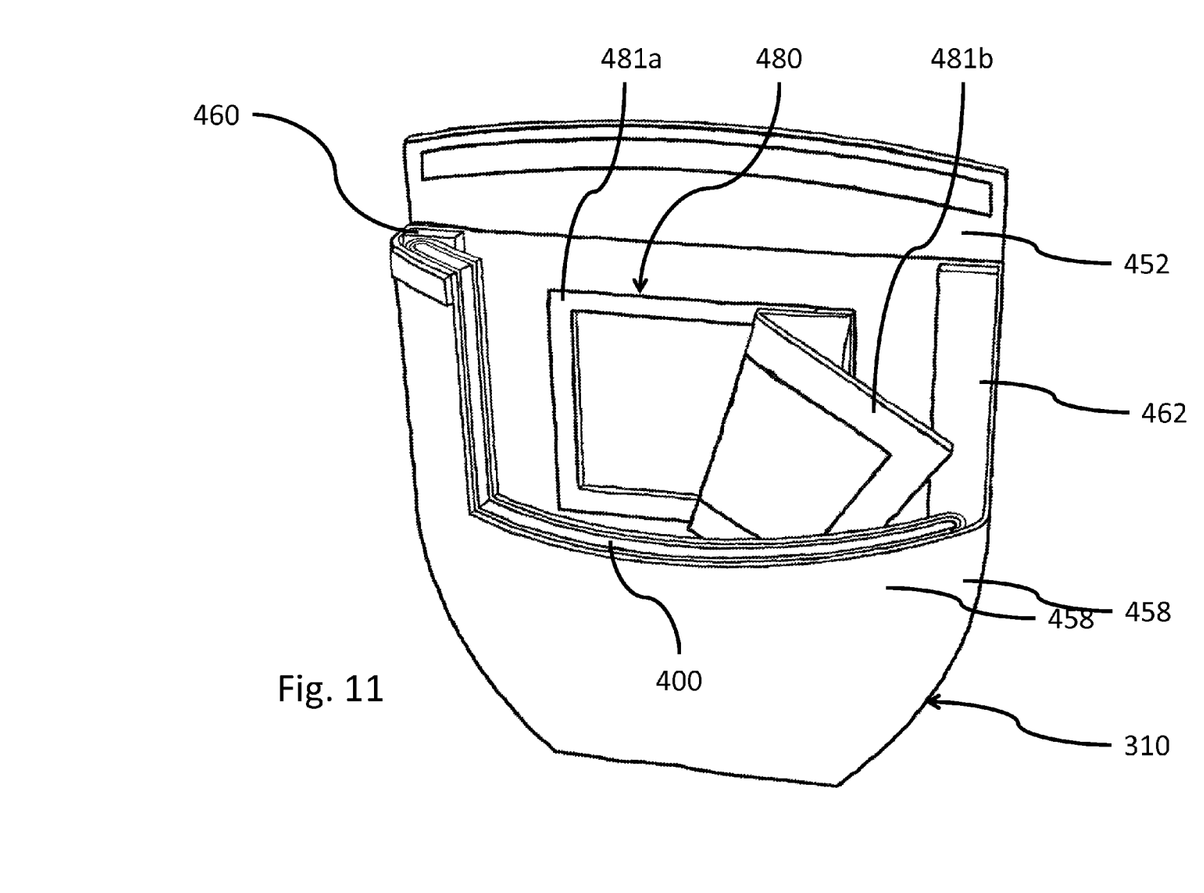
FIG. 11 is a perspective view of the compartment of FIG. 8 with a portion cut away to illustrate the interior window in an open position.

Referring to FIGS. 10 and 11, a window 480 is provided either in the compartment or in the garment adjacent to the compartment that allows for access to the region of the body behind the compartment where the port is implanted. The window 480 permits medical personnel to access the port for treatment purposes without requiring the patient to remove the garment. In the embodiment shown, the window 480 is a flap of material similar to the material used to form the compartment 310 or the material used to fabricate the garment. The window 480 may be removably secured to the compartment 450 or garment 300, such that the window can be opened and closed, or removed to permit access to the body area where the port is implanted. Conventional removable securing techniques, such as Velcro® hooks 481a and Velcro® loops 481b, may be used to removably secure the cover to the compartment or garment.

With certain illustrated embodiments described above, it is to be appreciated that various non-limiting embodiments described herein may be used separately, combined or selectively combined for specific applications. Further, some of the various features of the above non-limiting embodiments may be used without the corresponding use of other described features. The foregoing description should therefore be considered as merely illustrative of the principles, teachings and exemplary embodiments of this invention, and not in limitation thereof.

While described as an arched structure, the port shield described in the embodiments above may be in other forms, dimensions or curved shapes that dissipate energy from the port shield to sides of the shield and to areas of the body away from the port to provide suitable protection for an implanted port. The port shield may also include ventilation holes that pass entirely through the protective device to improve the comfort of the user, especially during sporting activities.

It is also to be understood that the above-described arrangements are only illustrative of the application of the principles of the illustrated embodiments. Numerous modifications and alternative arrangements may be devised by those skilled in the art without departing from the scope of the illustrated embodiments, and the appended claims are intended to cover such modifications and arrangements.

What is claimed is:

1. A protective device for surgically implanted ports, comprising:
   a port shield having a first side support, a separate second side support, and an arched structure with a crown between the first and second side supports; and
   at least one impact absorption layer positioned along the first side support and at least one impact absorption layer positioned along the second side support, such that energy from an impact to the port shield can be dissipated along a surface of the port shield to the two side supports and at least partially absorbed by the at least one impact absorption layer along the first and second side supports.

2. The protective device according to claim 1, wherein the port shield is made of plastic.

3. The protective device according to claim 1, wherein the at least one impact absorption layer is made of foam.

4. A protective device for surgically implanted ports, comprising:

a port shield having a first side support, a separate second side support, and an arched structure with a crown between the first and second side supports;

a padded layer secured to an inner surface of the port shield; and at least one impact absorption layer positioned on a portion of the padded layer along the first side support and at least one impact absorption layer positioned on a portion of the padded layer along the second side support, such that energy from an impact to the port shield can be dissipated along a surface of the port shield to the two side supports and at least partially absorbed by the portions of the padded layer along the first and second side supports and the at least one impact absorption layer along the first and second side supports.

5. The protective device according to claim 4, wherein the port shield is made of plastic.

6. The protective device according to claim 4, wherein the at least one impact absorption layer is made of foam.

7. The protective device according to claim 4, wherein the padded layer is made of foam.

8. A protective system for surgically implanted ports, comprising:

a port shield having a first side support, a separate second side support, and an arched structure with a crown between the first and second side supports; and a compartment having a sleeve configured and dimensioned to receive the port shield, at least two impact absorption members positioned within the compartment such that one impact absorption member is adjacent one side support and between a body when worn by a patient and the port shield.

9. The protective system according to claim 8, wherein the compartment has a cover.

10. The protective system according to claim 8, wherein the port shield is made of plastic.

11. The protective system according to claim 8, wherein the compartment is made of a material used to fabricate garments.

12. The protective system according to claim 11, wherein the compartment is attached to a garment and the compartment material is the same as the material used to fabricate the garment.

13. The protective system according to claim 11, wherein the compartment is integrally formed into a garment.

14. The protective system according to claim 8, wherein the compartment has a window to permit access to an area of a body when worn.

* * * * *